US012594382B2

(12) United States Patent
Moles et al.

(10) Patent No.: US 12,594,382 B2
(45) Date of Patent: Apr. 7, 2026

(54) ADAPTOR FOR A MEDICAMENT DELIVERY DEVICE AND A RELATED METHOD

(71) Applicant: The University of Sydney, New South Wales (AU)

(72) Inventors: Rebekah Jane Moles, New South Wales (AU); Philip Boughton, New South Wales (AU); Carl Schneider, New South Wales (AU); Timothy Chen, New South Wales (AU); Lyndal Trevena, New South Wales (AU); Henry Pleass, New South Wales (AU); Seamus Thomson, New South Wales (AU); Jennifer Fraser, New South Wales (AU); Andrew Mclachlan, New South Wales (AU)

(73) Assignee: The University of Sydney, New South Wales (AU)

( * ) Notice: Subject to any disclaimer, the term of this patent is extended or adjusted under 35 U.S.C. 154(b) by 931 days.

(21) Appl. No.: 17/595,016

(22) PCT Filed: May 20, 2020

(86) PCT No.: PCT/AU2020/050495
§ 371 (c)(1),
(2) Date: Nov. 5, 2021

(87) PCT Pub. No.: WO2020/232503
PCT Pub. Date: Nov. 26, 2020

(65) Prior Publication Data
US 2022/0211949 A1 Jul. 7, 2022

(30) Foreign Application Priority Data
May 20, 2019 (AU) ................................ 2019901707

(51) Int. Cl.
A61M 5/315 (2006.01)
A61J 7/00 (2006.01)
A61J 7/02 (2006.01)

(52) U.S. Cl.
CPC ........ A61M 5/31536 (2013.01); A61J 7/0053 (2013.01); A61J 7/0076 (2013.01);
(Continued)

(58) Field of Classification Search
CPC .......... A61M 5/31536; A61M 5/31591; A61M 2005/3154; A61M 5/31595;
(Continued)

(56) References Cited

U.S. PATENT DOCUMENTS 3,610,241 A * 10/1971 LeMarie ............. A61M 5/1782
604/407
4,073,321 A * 2/1978 Moskowitz ......... A61M 5/1782
141/27
(Continued)

FOREIGN PATENT DOCUMENTS

EP 2898913 A1 7/2015
WO 2003004080 1/2003

OTHER PUBLICATIONS

Written Opinion and International Search Report issued in International Application No. PCT/AU2020/050495 on Nov. 26, 2020.
(Continued)

*Primary Examiner* — William R Carpenter
*Assistant Examiner* — Robert F Allen
(74) *Attorney, Agent, or Firm* — Amster, Rothstein & Ebenstein LLP

(57) ABSTRACT
The invention provides an adaptor for a medicament delivery device is configured to enable a set dosage of a medicament to be drawn into and/or expelled from the device, the adaptor including: a body configured to be coupled to the
(Continued)

device; an attachment portion movable with respect to the body and configured for attachment with a first part of the device; an engaging portion movable with the attachment portion; and a receiver configured to receive a movement constraint guide (MCG) and facilitate engagement between the engaging portion and the MCG; wherein the MCG includes one or more physical features defining at least an aspect of the set dosage; and wherein activation of said first part of the device to draw and/or expel the medicament is stopped when the set dosage is reached by engagement between the engaging portion and at least one of the one or more physical features of the MCG. The invention thus allows ready control of one or more aspects of dosage administration, which can be the amount of a dose and/or or the repeats of a dose.

14 Claims, 12 Drawing Sheets

(52) U.S. Cl.
CPC ............ *A61J 7/02* (2013.01); *A61M 5/31568* (2013.01); *A61M 5/31591* (2013.01); *A61M 5/31595* (2013.01); *A61M 2005/31508* (2013.01); *A61M 2005/3154* (2013.01); *A61M 2205/3334* (2013.01); *A61M 2205/3379* (2013.01); *A61M 2205/584* (2013.01); *A61M 2205/6009* (2013.01); *A61M 2205/6072* (2013.01); *A61M 2205/6081* (2013.01); *A61M 2209/04* (2013.01)

(58) Field of Classification Search
CPC ...... A61M 2205/581; A61M 2205/583; A61M 5/31568; A61M 2005/31508; A61M 5/31501; A61M 5/3157; A61M 2205/582; A61M 2205/3334; A61J 7/0053; A61J 7/0076; A61J 7/02
See application file for complete search history.

(56) References Cited

U.S. PATENT DOCUMENTS

| | | | | | |
|---|---|---|---|---|---|
| 4,267,846 | A | * | 5/1981 | Kontos | A61B 5/153 604/220 |
| 4,444,335 | A | * | 4/1984 | Wood | A61M 3/00 222/43 |
| 4,475,905 | A | * | 10/1984 | Himmelstrup | A61M 5/31551 604/263 |
| 4,546,859 | A | * | 10/1985 | Newman | A61M 5/31555 604/209 |
| 4,563,178 | A | * | 1/1986 | Santeramo | A61M 5/1782 141/27 |
| 5,344,409 | A | * | 9/1994 | Ennis, III | A61M 5/31591 604/210 |
| 5,582,591 | A | * | 12/1996 | Cheikh | A61P 7/04 604/28 |
| 5,975,355 | A | * | 11/1999 | Cecala | A61M 5/31591 222/283 |
| 6,770,056 | B2 | * | 8/2004 | Price | G01F 11/023 604/207 |
| 7,611,495 | B1 | * | 11/2009 | Gianturco | A61M 5/3135 604/207 |
| 8,915,889 | B2 | * | 12/2014 | Cox | A61M 5/31545 604/110 |
| 8,945,069 | B2 | * | 2/2015 | Plumptre | A61M 5/31551 604/207 |
| 11,097,061 | B2 | * | 8/2021 | Gerlett | A61M 5/3153 |
| 2005/0137532 | A1 | * | 6/2005 | Rolla | A61M 5/31595 604/218 |
| 2005/0215955 | A1 | * | 9/2005 | Slawson | A61M 5/3129 604/192 |
| 2009/0043253 | A1 | * | 2/2009 | Podaima | G16H 10/60 604/67 |
| 2009/0093773 | A1 | * | 4/2009 | Toraishi | A61M 5/31536 604/246 |
| 2011/0172640 | A1 | * | 7/2011 | Cronenberg | A61M 5/31595 604/209 |
| 2012/0245530 | A1 | * | 9/2012 | Oden | A61M 5/31525 604/189 |
| 2013/0110054 | A1 | | 5/2013 | Raab et al. | |
| 2014/0180217 | A1 | * | 6/2014 | Kuczek | F04B 49/14 604/208 |
| 2014/0180245 | A1 | * | 6/2014 | Wong | A61M 5/3156 604/189 |
| 2014/0350516 | A1 | * | 11/2014 | Schwab | A61M 5/31595 604/209 |
| 2015/0157801 | A1 | * | 6/2015 | Tran | A61M 5/31591 604/208 |
| 2017/0224923 | A1 | * | 8/2017 | Cronenberg | A61M 5/31555 |
| 2018/0043105 | A1 | * | 2/2018 | Nazzaro | A61M 5/31568 |
| 2018/0078710 | A1 | * | 3/2018 | Pedde | A61M 5/31535 |
| 2018/0126085 | A1 | * | 5/2018 | Bowman | A61M 5/31595 |
| 2018/0236183 | A1 | * | 8/2018 | Chang | A61M 5/502 |
| 2018/0280622 | A1 | * | 10/2018 | Li | A61M 5/31563 |
| 2019/0355463 | A1 | * | 11/2019 | Gardner | G16H 40/63 |
| 2022/0280389 | A1 | * | 9/2022 | Pheng | G01F 11/06 |
| 2022/0347056 | A1 | * | 11/2022 | Ricci | A61M 5/31591 |
| 2023/0233772 | A1 | * | 7/2023 | Pedde | A61J 1/22 604/232 |

OTHER PUBLICATIONS

Extended European Search Report (EESR) issued in Application No. 20810397, dated Jan. 9, 2023.
Australian Examination Report issued to Patent Application No. 2020280117, dated Jun. 14, 2022 (4 pages).

* cited by examiner

ADAPTOR FOR A MEDICAMENT DELIVERY DEVICE AND A RELATED METHOD

CROSS-REFERENCE TO RELATED APPLICATIONS

This application is a U.S. national stage entry under 35 U.S.C. § 371 of PCT International Patent Application No. PCT/AU2020/050495, filed May 20, 2020, which claims priority to Australian Patent Application No. 2019901707, filed May 20, 2019, the contents of which are incorporated herein by reference in their entirety.

FIELD OF THE INVENTION

The present invention relates to medication management. In particular, it relates to an adaptor for a medicament delivery device such as a syringe, the adaptor configured to enable one or more set dosages of a medicament to be drawn into and/or expelled from the device.

BACKGROUND OF THE INVENTION

Critically unwell neonates are the most vulnerable population in terms of medication dose errors. Studies have shown that medication errors with the potential to cause significant harm are three times more likely in neonatal intensive care units than in adult wards. Due to the increased need for dose calculations, dilution and manipulation of medicines, a substantial proportion of preventable dose errors are reported to be 10 and 100 fold errors. In fact, a study conducted in 2000 showed that 8% of dosing errors in a paediatric hospital were 10-fold in magnitude and another study highlighted that 31% of prescriptions in a neonatal unit were for doses less than 10% of the contents of the vial and 4.8% are for doses less than 1% of the vial, demonstrating just how easy it is to give a fatal dose to a vulnerable neonate in this clinical environment.

Syringe dosing errors generally arise in two areas, being pharmacy dispensing of the dose and drawing of the dose into the syringe.

To date, technological innovations to reduce dose errors in neonates have focused on infusion rate, along with some simple physical stroke limiters for use with syringes. However there is no complete system that can reduce errors at the calculation, dispensing and administration stages of liquid dose administration. Even the most advanced (cloud-integrated) infusion pump systems used in some hospitals can be mistakenly overridden in the ward without controls or immediate traceability.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In one aspect, the present invention provides an adaptor for a medicament delivery device, the adaptor configured to enable a set dosage of a medicament to be drawn into and/or expelled from the device, the adaptor including: a body configured to be coupled to the device; an attachment portion movable with respect to the body and configured for attachment with a first part of the device; an engaging portion movable with the attachment portion; and a receiver configured to receive a movement constraint guide (MCG) and facilitate engagement between the engaging portion and the MCG; wherein the MCG includes one or more physical features defining at least an aspect of the set dosage; and wherein activation of said first part of the device to draw and/or expel the medicament is stopped when the set dosage is reached by engagement between the engaging portion and at least one of the one or more physical features of the MCG.

Advantageously, the present invention allows for a controlled dosage of fluid to be drawn in and/or expelled from the medicament delivery device, thereby substantially reducing the possibility of delivering a dosage of medicament that is not commensurate with the set dosage, particularly as it pertains to limiting the possibility of an overdose. This is achieved by using the one or more physical features of the MCG to limit the movement of the first part of the device.

The medicament delivery device is preferably a syringe for delivery of a fluid medicament, said first part of the device being a syringe plunger, activation of said first part of the device being movement of the syringe plunger.

In an alternative form, the medicament delivery device is a receptacle for delivery of medicament in solid (or part-solid) form, such as pills, capsules or tablets, said first part of the device comprising a mechanism to dispense the medicament elements in prescribed quantities, activation of said first part of the device being operation of said dispensing mechanism.

The MCG is preferably a planar element, such as a card of rectangular or other suitable form, the receiver having a complementary shaping to receive said element. The planar element may be flat or of curved form, such as arcuately curved in a part-cylindrical form. The MCG may be flexible if desired, allowing it to be positioned in the receiver through manipulation and flexion.

Alternatively, the MCG may take any other appropriate form, provided it is able to interact with the engaging portion to selectively limit the movement of the attachment portion and hence activation of the first part of the device. In a very simple form, for example, the MCG may be a block of a suitable material (such as a rectangular prism) which can be inserted into the receiver, the block of a particular dimension selected to limit movement of the engaging portion beyond a certain point. As will be understood, the MCG acts as a 'key', used to unlock the required medicament dosage from the device. The MCG may carry or be formed with a track providing said one or more physical features for guiding movement of a part of said engaging portion and thus movement of said first part of the device. In one form, the engaging portion and the attachment portion may be provided by a single unit, either an integral unit or an assembly of parts.

The set dosage may be a single dose or a prescribed dosing regime. In the latter case the MCG is configured to delimit more than one dose.

In one embodiment, the MCG may carry or be formed with a plurality of tracks. For example, the MCG may include a first track having said one or more physical features for guiding movement of a part of said engaging portion and thus movement of said first part of the device, and may also include a second track having one or more additional physical features configured to afford control of (and, optionally, and indication of) a number of doses of the medicament drawn and/or expelled.

In an embodiment, the engagement portion comprises an engaging element configured to be biased towards the MCG, and thereby allow the engaging element to engage the one or more physical features of the MCG when the MCG is suitably positioned in the receiver. The engaging element is preferably biased by a suitable fitted spring.

As the user is drawing and/or expelling the medicament from the medicament delivery device, the movement of the first part is stopped when engagement between the engaging portion and the one or more physical features of the MCG takes place. This indicates that the set dosage has been reached.

In another embodiment, the adaptor includes a second engaging portion movable in relation to the first engaging portion and configured to engage one or more additional physical features of the MCG. Engagement between the second engaging portion and the one or more additional physical features of the card may provide guidance to the number of dosages that can be administered (as well as, preferably, an indication of the number of dosages that have been administered).

Accordingly, in one form, engagement between the second engaging portion and the one or more additional physical features of the MCG may preclude further activation of said first part of the device to draw and/or expel the medicament when the set number of dosages to be administered has been reached. Preferably, the second engaging portion comprises a second engaging element configured to be biased towards the MCG, and thereby allow the second engaging element to engage the one or more additional physical features of the MCG when the MCG is suitably positioned in the receiver. The second engaging element is preferably biased by a biasing means, such as a spring.

In an embodiment, the engaging portion is adapted to be directly coupled to the attachment portion. This provides a simplified arrangement, whereby movement of the attachment portion, directly translates into movement of the engaging portion.

The one or more physical features (and, where applicable, the one or more additional physical features) may be protrusions or recesses on a surface of the MCG that provides abutment surfaces for the engaging portion. As discussed above, the one or more physical features may take the form of a track or tracks for guiding movement of said engaging portion, which may be a through-slot or a slot-like recess in the MCG. In an embodiment, the physical features include one or more frangible portions. When the engaging portion engages a frangible portion of the MCG, the frangible portion is ruptured. The MCG of this embodiment is therefore a consumable part that can be replaced by another MCG after is has been used. The rupturing of the frangible portions can provide an indication to a user that that the set dosage has been drawn and/or expelled from the medicament delivery device.

Alternatively, the MCG may be re-usable, i.e. not consumable after a single use. For example, a given MCG may be configured to provide a fixed set dosage when used. A user may use such a MCG whenever they intend to administer the fixed dosage. In another embodiment, the MCG may be adaptable to provide a desired dosage for a specific patient.

The one or more physical features (and, where applicable, the one or more additional physical features) of the MCG may define the set dosage in different forms. In one embodiment, the one or more physical features may be a defined pathway, wherein the path defines the amount of movement of the first part and thus the amount of medicament drawn into and/or expelled from the medicament delivery device. The pathway may alternatively or in addition define a plurality of set dosages. In one embodiment, the MCG may include multiple pathways, each pathway configured to engage a respective engaging portion and to define a set dosage.

In an embodiment, the MCG may be in the form of a punch card having one or more indications thereon for use in selecting the set dosage. The set dosage may be selected by marking or punching the punch card at or adjacent one or more of said indications.

In an embodiment, the first engaging portion is configured to move along a first track of the MCG and the second engaging portion is configured to move along a second track of the MCG. The first track may define a dosage volume of the set dosage and the second track may define a number of dosages of the set dosage.

In an embodiment, the adaptor includes a retaining structure movably mounted to the body. Preferably, the retaining structure is mounted adjacent the second track. Preferably, the retaining structure is arranged to constrain the second engaging portion to incremental movement relative to the first engaging portion. In one form, the retaining structure is in the form of a sawtooth rack.

It is preferred that the MCG be specific for a given patient. For example, the MCG may include one or more smart features, such as an encoded element configured to provide patient specific information to an external device. The external device may be a computer, a smartphone, or the like. The patient specific information may include dosage information, identification information, etc.

In another aspect, the present invention provides a method for controlling medicament administration, including the steps of: recording prescription information regarding a medicament, a dosage and a patient to whom the medicament is to be administered; providing for production of a movement constraint guide (MCG), the MCG including: one or more physical features defining at least an aspect of the dosage; and one or more readable identification features including one or more pieces of the prescription information; recording administration information associated with the use of the MCG with a medicament delivery device; the administration information including: data produced by reading said one or more readable identification features from the MCG; and an indication of delivery of the dosage of the medicament to the patient by way of the medicament delivery device operating under constraints imposed by the interaction of the physical features of the MCG with the medicament delivery device.

In another aspect, the present invention provides a non-transitory computer-readable medium containing instructions which when executed on a processor performs the method of the previous aspect.

Thus, the present invention can provide an integrated dose management and hardware governing system, a generally mechanical recording function and optical recognition module for safely delivering medicaments.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
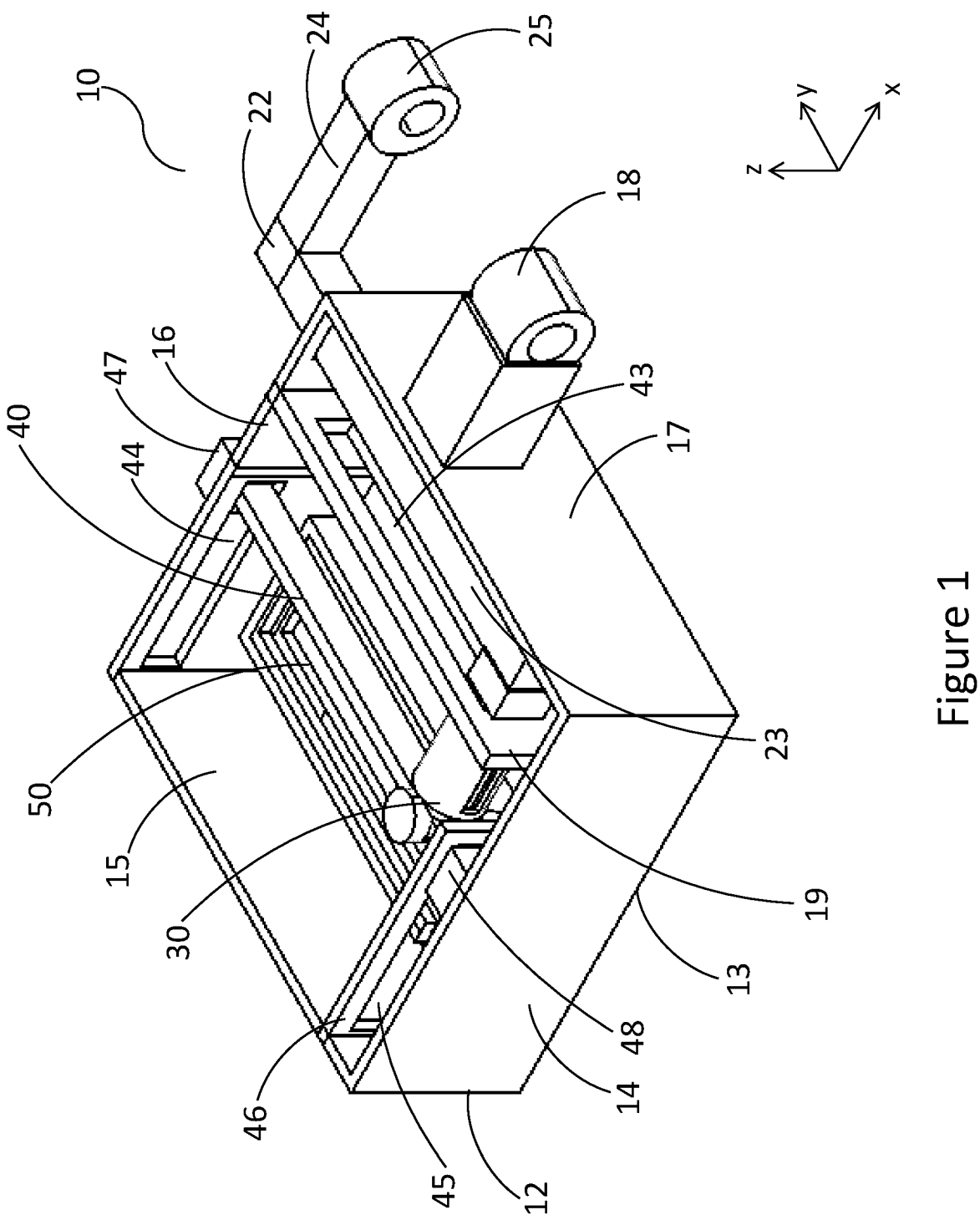
FIG. 1 is an upper isometric view of an adaptor in accordance with an embodiment of the present invention.
Figure 2:
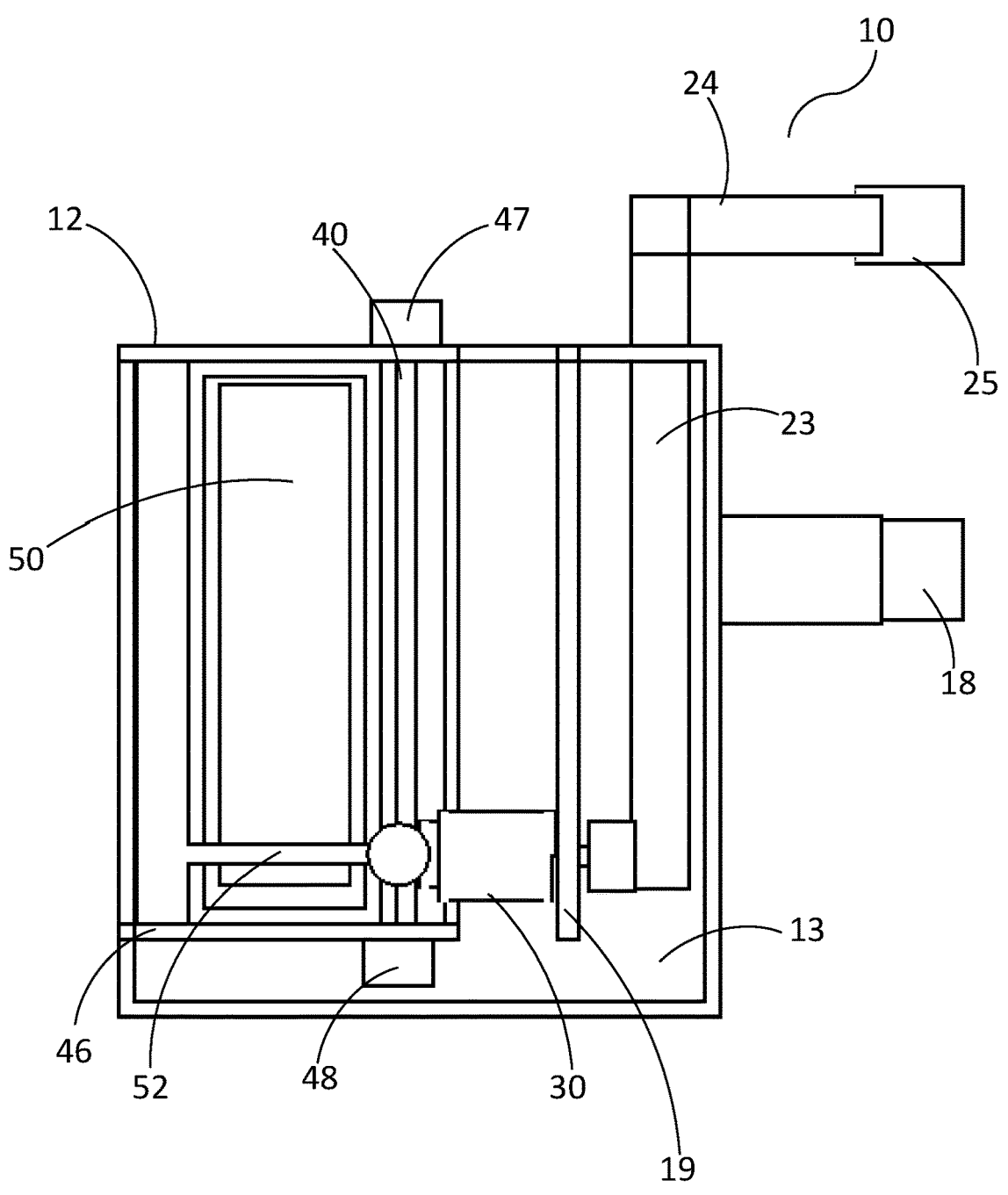
FIG. 2 is an upper plan view of the adaptor of FIG. 1.

FIGS. 1 and 2 show a first embodiment of an adaptor 10 configured for coupling to a syringe (not shown). The adaptor comprises a housing 12, with a planar base 13 arranged along the longitudinal direction of the syringe, sidewalls 14, 15, 16, 17 extending perpendicularly therefrom, and a top cover (not shown). As described herein, the longitudinal direction of the syringe is parallel with the y-axis of housing 12 as shown. The x-axis is transverse to the longitudinal direction and parallel with the planar base 13. The z-axis is perpendicular to the x and y-axis, i.e. sidewalls 14, 15, 16, 17 extend in the z-direction.

Extending perpendicularly outwardly from sidewall 17 in the x-direction is flange coupling portion 18, which is adapted to attach to or support the flange of the barrel of the syringe. The flange coupling portion 18 provides support for the housing 12 when the barrel and plunger are moved relative to one another whilst the adaptor 10 is coupled to the syringe, as described in further detail below. The end of the flange coupling portion 18 distant from housing 12 has a circular bore as shown, dimensioned for receiving the barrel of the syringe.

The adaptor 10 is connected to a plunger of the syringe by a substantially L-shaped linking member 22, which at one end is received within housing 12 and at the other end is connectable to the plunger. Linking member 22 includes a first leg 23 extending longitudinally in the y-direction and a second, exterior leg 24 connected thereto and extending transversely in the x-direction away from housing 12. First leg 23 passes through a complementary shaped aperture in sidewall 16 and connects within housing 12 to pin assembly 30, as explained below. The end of second leg 24 away from housing 12 is provided with a plunger coupling portion 25 adapted to connect to or bear against the plunger of the syringe, plunger coupling portion 25 provided with a circular bore in line with the bore of flange coupling portion 18. In this way, movement of the plunger in the y-direction (with the syringe barrel held by flange coupling portion 18) results in a corresponding movement of the linking member 22 in the y-direction.

Figure 3:
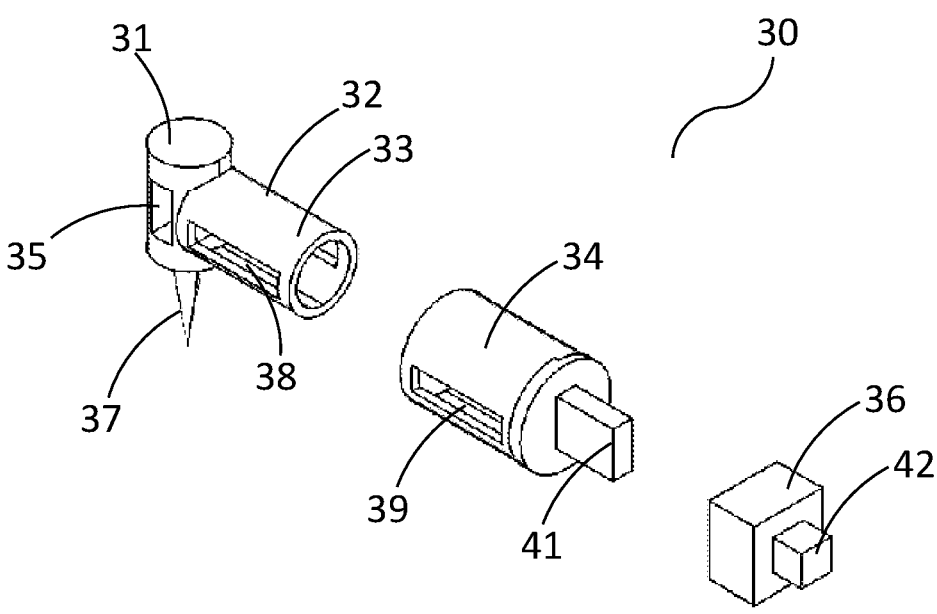
FIG. 3 is an upper isometric exploded view of a pin assembly in accordance with an embodiment of the present invention.
Figure 4:
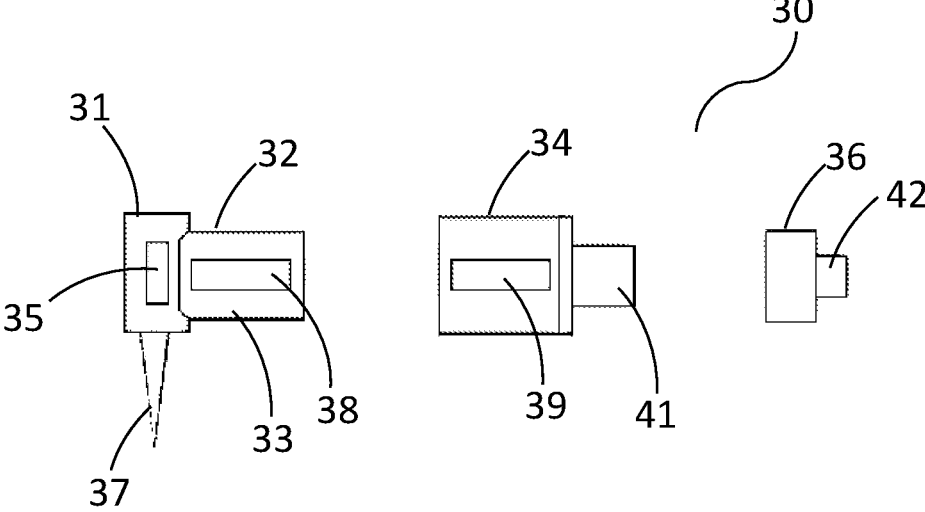
FIG. 4 is an front exploded view of the pin assembly of FIG. 3.

The pin assembly 30 is illustrated in FIGS. 3 and 4. Pin assembly 30 is arranged in the x-direction and comprises three parts, a head part 32, a body part 34 and a cap part 36. Head part 32 is integrally formed from two generally tubular portions connected in a substantially T-shape, with a first tubular portion 31 forming the top bar of the T and a second tubular portion 33 forming the depending leg of the T. The first tubular portion 31 extends in the z-direction, having closed ends and a longitudinally-extending rectangular shaped through-hole 35 therethrough. Through-hole 35 is adapted to receive a sliding tracking bar 40, as detailed below. Projecting into the housing 12 from the closed end of first tubular portion 31 is a pin 37, configured to engage a track in a smart card 60 (see FIG. 5). Second tubular portion 33 extends in the x-direction, having an open end at the end furthest from the first tubular portion 31. A longitudinal rectangular shaped through-hole 38 is provided in second tubular portion 33.

Body part 34 is generally tubular in form, similar to that of the second tubular portion 33 of part 32, with an open end and a closed end. Body part 34 has an internal diameter complementary to the external diameter of portion 33 to receive the latter from its open end in a sliding manner, the two configured to house therebetween a suitably sized compression spring (not shown), as discussed below. In the assembled state of pin assembly 30, a locking pin (not shown) extends through through-holes 38 and 39 to prevent separation of the parts. Hence, as will be understood, body parts 32 and 34 are connected in a telescoping arrangement in their longitudinal direction, the compression spring urging them apart and the locking pin precluding their separation.

Extending in the x-direction externally from the closed end of body part 34 is a shaped projection 41 configured to be received in a corresponding recess in the cap part 36. When pin assembly 30 is appropriately positioned inside housing 12, the projection 41 extends from the body part 34 and through a channel 43 in an internal divider wall 19, which as shown (see FIG. 1) extends from planar base 13 of housing 12 parallel to sidewalls 15 and 17 (ie. lying in the yz plane). Projection 41 is received by the cap part 36 on the other side of the divider wall 19. On the side opposed to the recess, cap part 36 also includes a central shaped projection 42 to be received in a corresponding recess at the distal end of first leg 23 of linking member 22. Therefore, by way of these connections, linking member 22 and pin assembly 30 can move with one another in the y-direction, while the head part 32 can move relative the rest of pin assembly 30 in the x-direction.

Movement of pin assembly 30 in the x-direction is facilitated by sliding tracking bar 40. Bar 40 is an elongate member extending in the y-direction that passes through the through-hole 35 of tubular portion 31 of the pin assembly head part 32. A further internal divider wall 46 extends from planar base 13 of housing 12 parallel and close to sidewall 14 (ie. lying in the xz plane). At its two ends, tracking bar 40 passes through long slots 44 and 45 in housing sidewall 16 and divider wall 46, respectively, as shown in FIG. 1. Long slots 44 and 45 are therefore parallel and coincident when viewed in the y-direction. Bar 40 is retained at each end by external caps 47,48, that bear against sidewall 16 and divider wall 46 respectively. Tracking bar 40 is therefore mounted to slide in the x-direction, thereby moving pin assembly head part 32 (including pin 37) in the x-direction.

The housing 12 includes a receiver 50 in the form of a rectangular plinth orientated in the xy plane, defined by standwalls as shown, sized to receive a smart card 60 (see FIG. 5), so to facilitate engagement of the smart card 60 with the pin 37. Receiver 50 includes a channel 52 through the plinth standwalls, which allows access of the pin 37 in the x-direction to the smart card 60 when positioned on the plinth.

Figure 5:
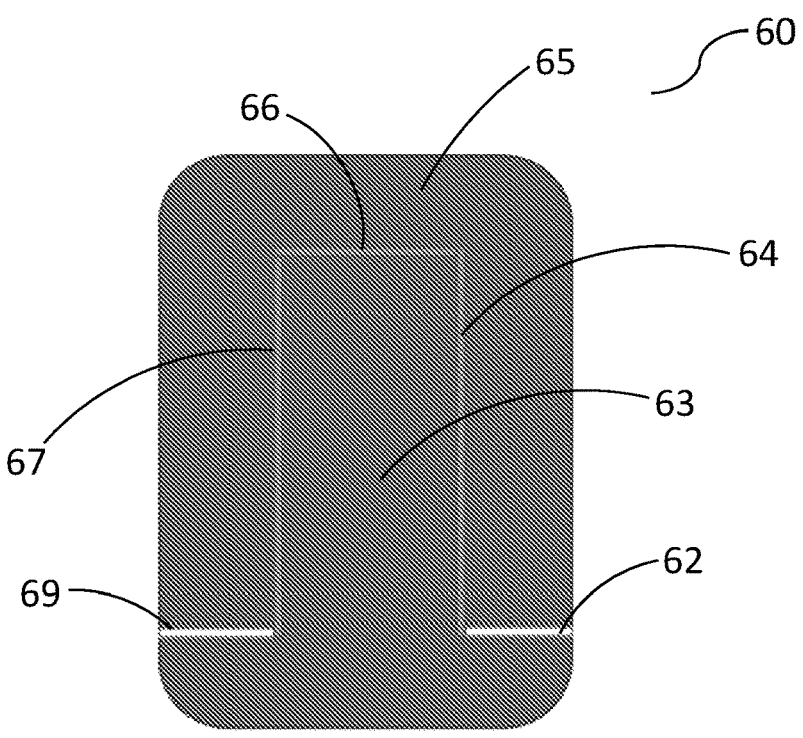
FIG. 5 is an upper plan view of a smart card in accordance with an embodiment of the present invention.

Turning to the smart card 60 shown in FIG. 5, this includes a track that defines a set dosage to be drawn into and expelled from the syringe. Smart card 60 has rounded corners as shown, and length and width dimensions to suit receiver 50. Directional references in relation to card 60 are made with reference to the same coordinate plane as used above with reference to housing 12, i.e. with card 60 positioned in receiver 50, lying in the xy plane with the long side of the card in the y-direction.

Figure 6:
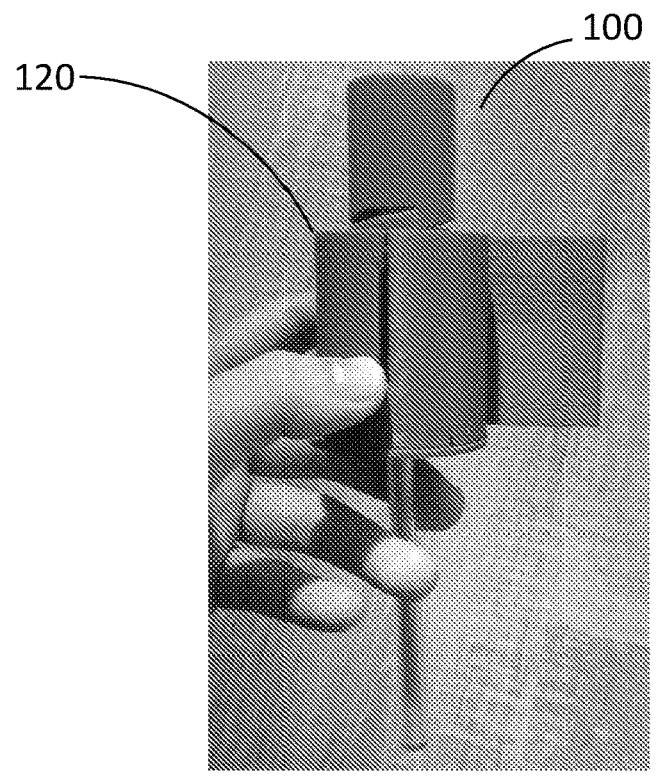
FIG. 6 is a front view of an upper assembly of an adaptor in accordance with another embodiment of the present invention.

Card 60 is formed from different pieces of paper material laminated together. The different material provides the card 60 with different physical features, which influences the movement of the pin 37 when it engages the card 60. For example, the card 60 includes both a combination of frangible portions, i.e. portions that rupture or tear when engaged by pin 37, and non-frangible portions, i.e. parts which do not rupture or tear when engaged by pin 37. The non-frangible portions thus constrain movement of the pin 37. The non-frangible portions include an inverted T-shaped portion 63 and an inverted U-shaped portion 65 which are connected to one another by frangible portions 64, 66, 67 as shown in FIG. 6. A person skilled in the art will appreciate that the different physical features of the card can be realised in many other ways. For example, the physical features may be in the form of protrusions on the card 60 that constrain movement of the pin 37. In another example, there may be no frangible portions, but instead the track may be covered by a foil, film or other marking that is visually and indelibly changed upon advancement of the pin along the track. For example, the track may be transparent, reflective, or revealing of a unique encoded background pattern. This can also provide the card 60 with an in-built security against forgery or digital methods to avoid traceability during use. The card may also have a visible smartphone scannable QR or bar code for ease of cross checking prior to use. The path on the card may also be scannable, embodying information relating to the dosage provided by the card 60. The engagement between the pin 37 and the card 60 is further explained below.

The card 60 includes an entry way 62, in the form of a slit, extending in the x-direction from the end of the card 60 that is nearest to the pin assembly 30. Entry way 62 provides an entrance for pin 37 to engage with the card 60. The pin 37 is configured to move along entry way 62 until it engages non-frangible portion 63, which stops movement of the pin 37. The pin 37 is then configured to move in the y-direction through frangible portion 64 until it engages non-frangible portion 65. The pin 37 is then again configured to move in the x-direction through frangible portion 66 until it engages another part of non-frangible portion 65, which stops further movement of the pin 37 in the x-direction. The pin 37 is then configured to move in the y-direction through frangible portion 67 until it engages another part of non-frangible portion 63, which stops further movement of the pin in the y-direction. Finally, the pin 37 is then configured to move in the x-direction along exit way 69 which, like entry way 62, is in the form of a slit extending in the x-direction from the end of the card 60 that is furthest from the pin assembly 30, until it exits the card 60, thereby bringing an end to the engagement between the pin 37 and the card 60.

It will be readily appreciated by a person skilled in the art that for the card 60 to adequately function, the card 60 must be structurally stable whilst pin 37 is moving through the path defined by the card 60. Thus, in some examples the card is made adequately thick relative to the depth of the frangible portions so as to avoid the card structurally failing during operation. In an alternative embodiment, the card 60 will not include frangible portions (as previously discussed), and thus the card must be able to suitably withstand any forces that act thereon in use (for example, by the pin 37).

A method of drawing and expelling liquid from the syringe will now be described. As the card 60 includes frangible portions 64, 66, 67, the card 60 is therefore a consumable component, meaning a new card is required for each use. Firstly, adaptor 10 is suitably connected to the syringe, with the plunger coupling portion 25 connected to the plunger of the syringe and the flange coupling portion 18 connected to the flange of the syringe. The sliding tracking bar 40 is to be held in the position shown in FIGS. 1 and 2. In this position, the pin assembly 30 is in a retracted position as the compression spring is compressed. This is because the sliding tracking bar 40 forces the head portion 32 of the pin assembly 30 in the x-direction away from the receiver 50. This leads to the compression spring housed within the second tubular portion 33 to be compressed and the second tubular portion 33 sliding further within body part 34. The compression spring thus stores potential energy and is now biased to provide a force in the x-direction towards the receiver 50.

In the next step, card 60 is received and secured within receiver 50. The physical features of the card 60 define the set dosage that is to be drawn and the set dosage that is to be expelled from the syringe. Sliding tracking bar 40 is then released. This causes the release of some potential energy in the compression spring and movement of the pin 37 through channel 52 in the receiver 50, and through entry way 62 of the card 60. Pin 37 is brought to a halt when it engages non-frangible portion 63 of the card 60.

The syringe is now ready to draw in the liquid that is to be administered to a patient. The user now proceeds to lift the plunger in the y-direction, thereby creating a pressure differential between the tip of the syringe and the inside of the barrel in order to draw liquid into the barrel. This movement of the syringe plunger leads to a corresponding movement in the y-direction of the linking member 22. As the linking member 22 is connected to pin assembly 30 through the connection between the cap part 36 and the first leg 23, the pin assembly 30 is also moved in the y-direction along the channel 43 of divider wall 19. This movement leads to the pin 37 rupturing the frangible portion 64 of the card 60 as it progresses along the path provided by the card 60 until the pin 37 engages the non-frangible portion 65. This engagement stops any further movement of the pin 37 and thus stops the user of the syringe moving the plunger any further upwards in the y-direction. Therefore, the dosage that can be drawn into the syringe barrel has been limited by the by the non-frangible portion 65 of the card 60.

Once the pin 37 engages the non-frangible portion 65, the pin 37 is presented with a frangible portion 66 in the x-direction towards receiver 50. As frangible portion 66 does not constrain the movement of the pin 37, and because of the biasing of the pin 37 in the x-direction towards the receiver 50, the pin 37 will move through the path of frangible portion 66 as the spring releases further potential energy, thereby rupturing frangible portion 66. In other words, once the pin 37 engages the non-frangible portion 65 (signifying the completion of the drawing in of liquid as defined by the set dosage provided by the card 60), the pin 37 is immediately urged in the x-direction towards the receiver 50 until the movement of the pin 37 is again halted by engaging another part of non-frangible portion 65.

Now the user may expel the liquid in the syringe. The user pushes the plunger downwards in the y-direction. This movement of the syringe plunger leads to a corresponding downward movement in the y-direction of the linking member 22. As the linking member 22 is connected to pin assembly 30, the pin assembly 30 is also moved downward in the y-direction along channel 43. This movement leads to the pin 37 rupturing the frangible portion 67 of the card 60 as it progresses along the path provided by the card 60 until the pin 37 engages another part of non-frangible portion 63. This engagement stops any further movement of the pin 37 in the y-direction and thereby prevents any further expelling of liquid. Therefore, the set dosage as defined by the card 60 has been administered to the patient.

Once the pin 37 engages the non-frangible portion 63, the pin 37 is presented with exit way 69 in the x-direction towards receiver 50. As exit way 69 does not limit the movement of the pin 37, and because of the biasing of the pin 37 in the x-direction towards the receiver 50, the pin 37 will move through the exit way 69 as the spring releases its remaining potential energy. Thus, pin 37 will be moved until it completely exits the card 60, thereby bringing to an end the engagement of the pin 37 with the card 60. The ruptured frangible portions of card 60 provide an indicator to the user that the set dosage has been administered, and that a new card 60 would be needed in order to administer further dosages to the patient (or any future patient).

Reference is now made to FIG. 6, which depicts an alternative embodiment of an adaptor 100 configured to be coupled to a syringe. The mechanism of drawing and expelling liquid using the adaptor 100 differs from that of the adaptor 10 as will be described below. However the principle of operation of adaptor 10 is identical to that of adaptor 100, the latter providing a more compact form of the device.

The adaptor 100 includes a base 113 (not shown in FIG. 6) providing a support for the barrel of a syringe and an upper assembly 120 providing a mechanism to drive the plunger of the syringe relative to the barrel.

Figure 7:
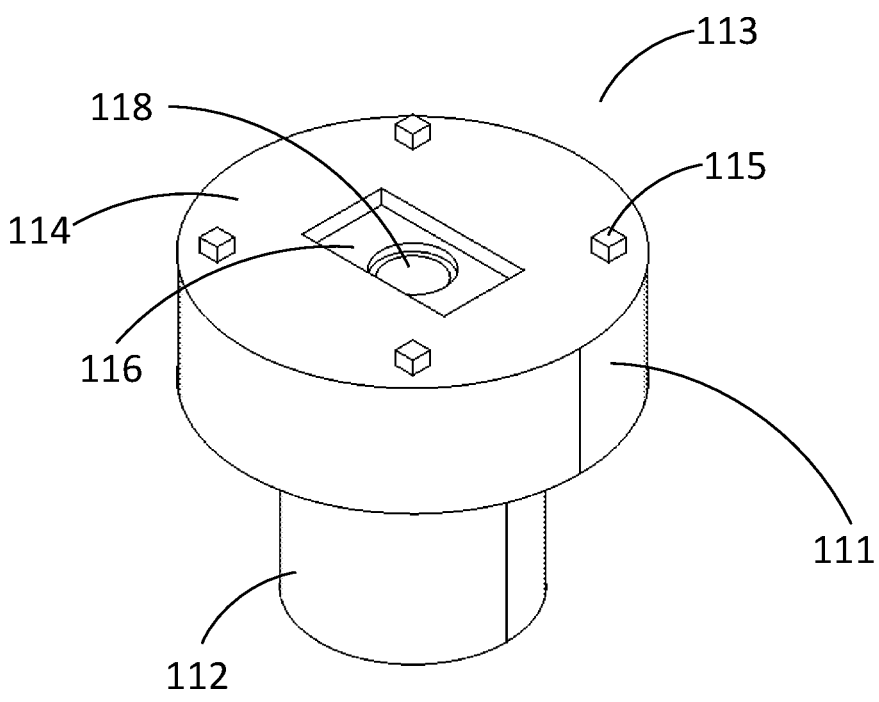
FIG. 7 is an upper isometric view of a base of an adaptor in accordance with another embodiment of the present invention.

As illustrated in FIG. 7, base 113 is integrally formed from two concentric, generally tubular portions joined as shown to form a substantially T-shape in side view, the bar of the T-shape provided by a first tubular portion 111 of larger diameter than the second tubular portion 112 (the leg of the T-shape). Base 113 has a through bore 118 extending through its axial centreline sized to receive the barrel of the syringe and to provide support therefor when the syringe plunger is moved relative to the barrel. Base 113 also comprises four spaced shaped locating protrusions projecting from its upper surface 114 close to its outer periphery, to be received by complementary apertures 144 in a portion of the upper assembly 120 (see FIG. 9). Upper surface 114 of base 113 further includes a recess 116 that surrounds through bore 118, shaped and sized to provide a seat for the flange of the syringe barrel. The depending second tubular portion 112 of base 113 provides a grip portion for a user, avoiding need for the user to hold the syringe barrel.

Figure 8:
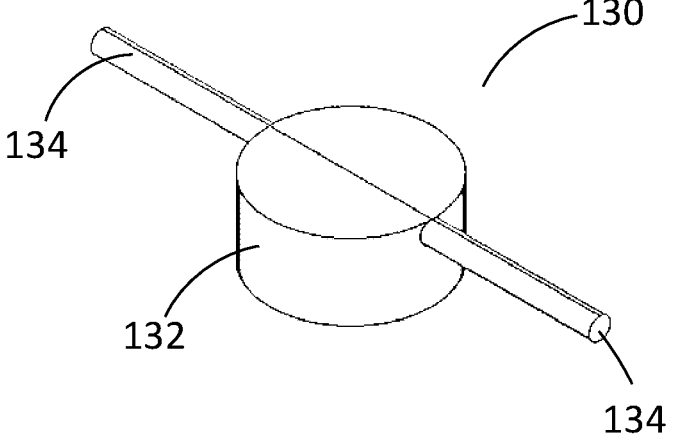
FIG. 8 is an upper isometric view of a pin assembly in accordance with another embodiment of the present invention.

The various components of upper assembly 120 will now be described with reference to FIGS. 8-12. A pin assembly 130 is configured to engage a card similar to card 60 (but of different dimensions) and to receive and engage the head of the syringe plunger to allow upward movement of the pin assembly 130 to pull up the syringe plunger and for the downward movement of the pin assembly 130 to push down the syringe plunger. More specifically, the pin assembly 130 includes a tubular portion 132 with a circumferential wall, a closed planar end and an opposed open end, the open end arranged to receive the flanged head of the syringe plunger. The open end of pin assembly 130 is configured to receive the head of the syringe plunger in a snap-fit arrangement. However, other connecting arrangements may also be employed as will be appreciated by a person skilled in the art. A shaft 134 is passed through a diametrical bore through tubular portion 132 such that its two ends protrude radially outwardly from diametrically opposed positions in tubular portion 132 close to the closed end, as shown in FIG. 8. In an alternative arrangement, not shown, the shaft 134 may be passed through a blind hole, whereby the shaft 134 protrudes radially outward from only one side of tubular portion 132. In either embodiment, as discussed further below, the end or ends of shaft 134 realises a tracking function similar to pin 37 of the first embodiment described above.

Figure 9:
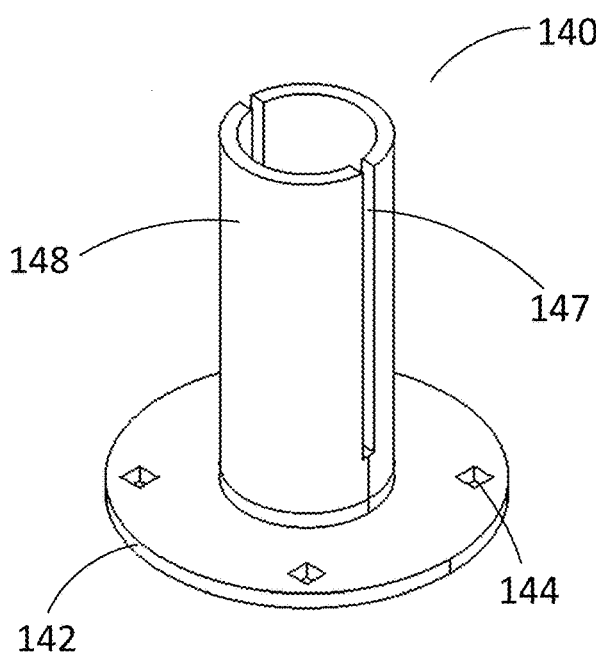
FIG. 9 is an upper isometric view of an inner longitudinal track component in accordance with another embodiment of the present invention.
Figure 10:
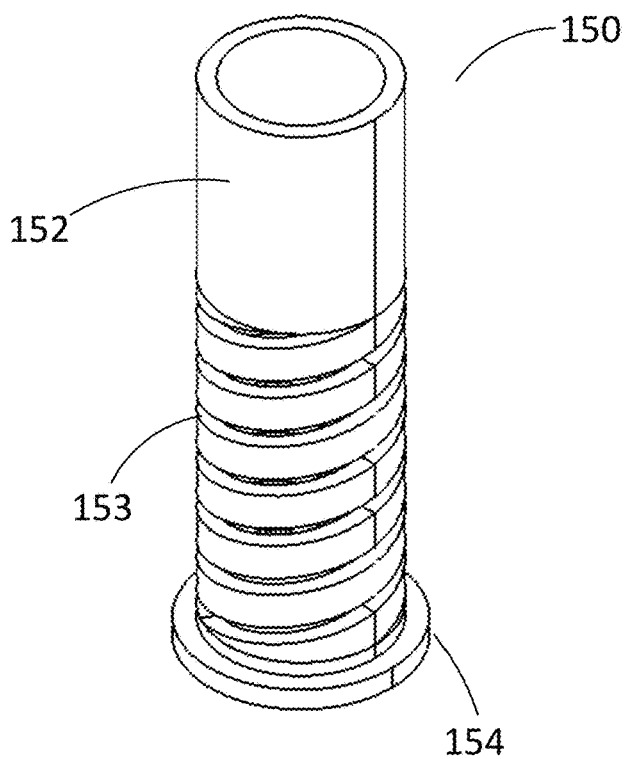
FIG. 10 is an upper isometric view of a helical track component in accordance with another embodiment of the present invention.

The upper assembly 120 further includes an inner longitudinal track component 140 as shown in FIG. 9, which comprises a cylindrical tube portion 148 integrally connected to a concentric disk-shaped base portion 142, the plane of the latter being perpendicular to the longitudinal direction of tube portion 148. Base portion 142 includes apertures 144 sized and positioned to receive the protrusions 115 of the base 113 of adaptor 100, and a central bore (not shown), coincident with the inner diameter of tube portion 148. When the inner longitudinal track component 140 is attached to base 113 the bore of base portion 142 is concentric with the through bore 118 of base 113, allowing the syringe plunger to move upwardly or downwardly within tube portion 148.

Tube portion 148 provides an inner linear pin track, the track provided by a pair of diametrically opposed slots 147 arranged in the axial direction running from the upper open end of the tube portion 148 to a point close to base portion 142, the slots acting as a guide for the projecting ends of the shaft 134 when pin assembly 130 is engaged with inner longitudinal track component 140 and moved in the longitudinal direction. Tube portion 148 has an inner diameter to accommodate the outer diameter of tubular portion 132 of pin assembly 130 to allow the pin assembly 130 to move upwardly and downwardly along the inner longitudinal track component 140, but to prevent any rotation between the two.

The upper assembly 120 further includes a helical track component 150 (FIG. 10) that is configured to be placed over the inner longitudinal track component 140 and to act as an outer sleeve for rotation relative to the inner longitudinal track component 140. Helical track component 150 comprises a tubular portion 152 with a base flange 154 as shown. Over a portion of the tubular portion 152 two helical slots 153 are provided, the slots starting from diametrically opposite positions close to base flange 154 and continuing for around 2/3 of the longitudinal extent of tubular portion 152. This longitudinal extent corresponds to the length of slots 147 once the helical track component 150 is positioned over the inner longitudinal track component 140 such that helical track base flange 154 sits on inner longitudinal track base portion 142. Like slots 147, helical slots 153 are sized to accommodate the projecting ends of the shaft 134. The upper end of the tubular portion 152 over which helical slot 153 does not extend provides a handle by which a user can rotate the helical track component 150 relative to inner longitudinal track component 140. As will be understood, when the pin assembly 130 is in place, rotation of helical track component 150 (and engagement between the projecting ends of shaft 134 with helical slots 153) will cause it to move in the longitudinal direction relative to the tubular track provided by the inner longitudinal track component 140.

The upper assembly 120 further includes an outer longitudinal track component 160 (see FIG. 11), designed to be placed over the helical track component 150, to act as an outermost sleeve around the inner longitudinal track component 140 and the helical track component. The outer longitudinal track 160 is seated on base portion 142 in the assembled adaptor 100, thus providing a chassis structure for support of the other components. Outer longitudinal track component 160 also acts as a card receiver, as discussed in more detail below.

Outer longitudinal track component 160 has a double-walled tubular form with an outer wall 162 and a concentric inner wall 164, providing an annular gap 163 therebetween. Gap 163 houses a spring means (not shown), the function of which will be described below. The outer and inner tubular walls 162, 164 are provided with diametrically opposed, angularly aligned longitudinal slots 166 as shown, running in the axial direction. The slot 166 of the inner tubular wall 164 is sized to accommodate the projecting ends of shaft 134 when the components are assembled together. The slot 166 of the outer tubular wall 162 can be provided with a clear outer window (not shown) that acts as a backing support for the ends of shaft 134 when it engages with the card, and allows observation by the user to check suitable engagement between the shaft 134 and the card. The material used for the window can be any suitable transparent or translucent material such as glass, plastic, etc.

Figure 11:
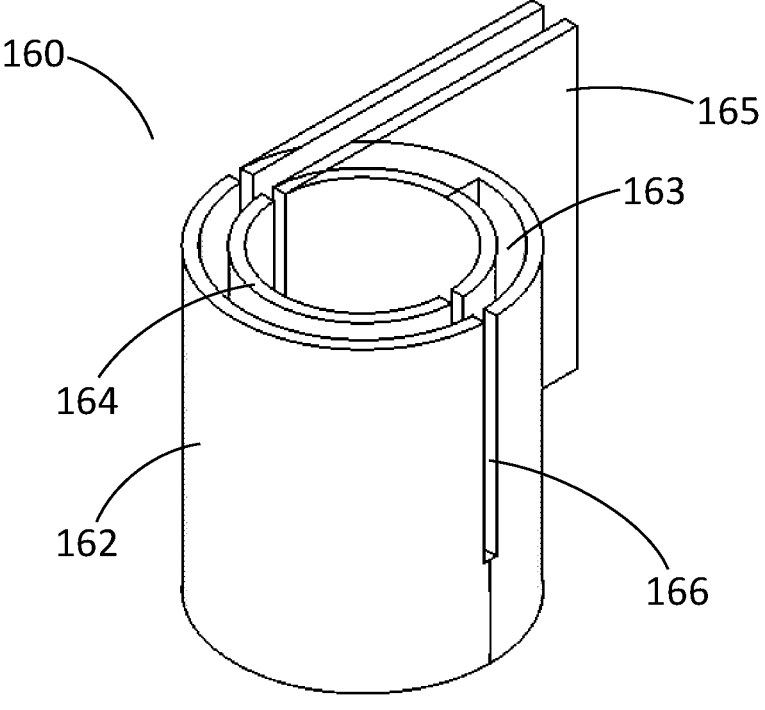
FIG. 11 is an upper isometric view of an outer longitudinal track component in accordance with another embodiment of the present invention.
Figure 12:
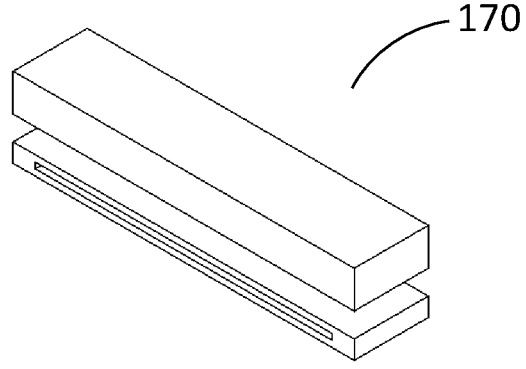
FIG. 12 is an isometric view of a card receiver insert part in accordance with another embodiment of the present invention.

As can be seen in FIG. 11, annular gap 163 extends only part of the angular extent of component 160, terminating in a radial end wall. At the other end, annual gap continues in a tangential direction in a straight channel provided by a pair of planar walls 165. A card receiver insert part 170 (FIG. 12) is attached to the outer ends of walls 165, providing an insert means for a card to be introduced into annular gap 163.

Figure 13:
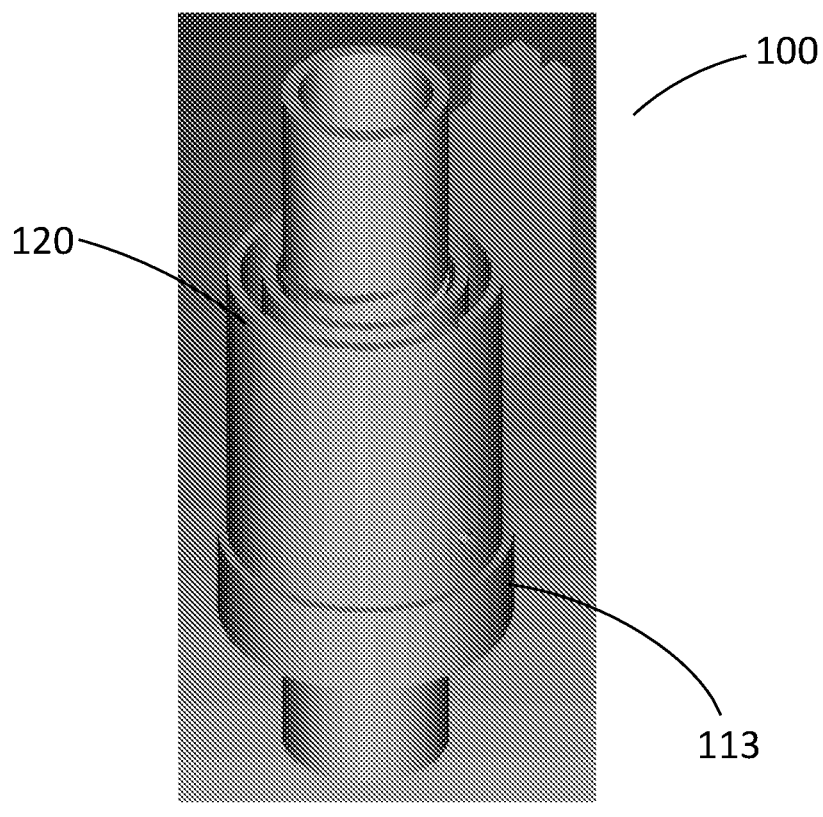
FIG. 13 is an upper isometric view of an assembled adaptor in accordance with another embodiment of the present invention.

FIG. 13 shows the upper assembly 120 positioned on base 113 (the syringe is not shown). To assemble the adaptor 100 with the syringe, the syringe barrel is passed through bore 118 in base 113 and barrel flange located in recess 116. The upper assembly 120 is then assembled and placed over the syringe plunger, with the head of the syringe plunger received in the tubular portion 142 of pin assembly 130 and the apertures 144 of inner longitudinal track component base portion 132 located over protrusions 115 of base 113. The card is then inserted through card receiver insert part 170 to be tangentially introduced into annular gap 163, to interact with the projecting ends of shaft 134 as described further below. As noted above, the card used for this embodiment of the invention may be of different dimensions to card 60, however it will take a generally similar form and the same reference numerals will be used when referring to parts of the card as used with reference to card 60. When the card is introduced through insert part 170, the card flexes to conform against the inner surface of the outer wall 162 and the outer surface of the inner wall 164, with the card urged into the gap 163 until shaft 134 passes through entry way 62, at which point portion 63 prevents further movement of the card relative to the shaft 134. The card is now seated snugly in annular gap 163. In this position, with the card engaged by shaft 134, the card is prevented from moving axially, and the spring means is biased to cause rotation of the card out of annular gap 163. The card can move circumferentially approximately 45-120°, corresponding to the arc of the length of the card.

Once the card has been inserted as described above, the syringe is ready to draw in the liquid medicament to be administered to a patient. The user begins by rotating the helical track component 150 clockwise, thereby rotating it relative to the inner and outer longitudinal track components 140, 160 and causing the projecting ends of shaft 134 to be urged axially upwardly, along slots 147 and 166 of the inner and outer longitudinal track components 140, 160 respectively. This movement of the projecting ends of shaft 134 is further constrained by engagement with portion 64 of the card and continues until the projecting ends of shaft 134 engage portion 65. Thus, a set dosage of liquid has now been drawn into the syringe. The spring means then urges the card outwardly so that portion 66 moves against the shaft 134 until the shaft 134 engages another part of portion 65.

To expel the liquid medicament, the helical track 150 is rotated anticlockwise relative to the inner and outer longitudinal track components 140, 160, causing the projecting ends of shaft 134 to be urged axially downwardly and passing along portion 67 until meeting another part of portion 63. Thus, a set dosage of liquid has now been expelled from the syringe. The spring finally continues to urge the card outwardly so that the card moves past shaft 134 through exit way 69. The card can now be removed from adaptor 100.

This embodiment can also employ a spring damping system for controlling draw and delivery rate. The spring damping system can assist in operation by smoothing the rotating action involved in drawing and expelling the medicament in order to mitigate against the formation of bubbles in the medicament or avoid leaks in the syringe plunger seal, particularly when dealing with thick liquid medicaments (which can otherwise cause dose inaccuracy). The spring means can be a torsion spring, and a damping element such as a pneumatic piston can be used, provided as a coupling between the syringe plunger and the pin assembly 130 and providing damping over (say) around 5-20 mm of travel. The piston can include an adjuster to control the rate of fluid flow into and out of the device, thereby controlling the rate of draw and expelling of the liquid medicament.

In the above described embodiment, where the card does not include frangible portions, the ends of shaft 134 can track along the card as a stylus in a fractional depth cut groove. In this case, the shaft 134 is permitted to exit the card by a tapering groove in the card that acts as a ramp, in combination with a trough feature on the inner surface of the outer wall 162 that removes the backing support provided for the shaft and card engagement.

Figure 14:
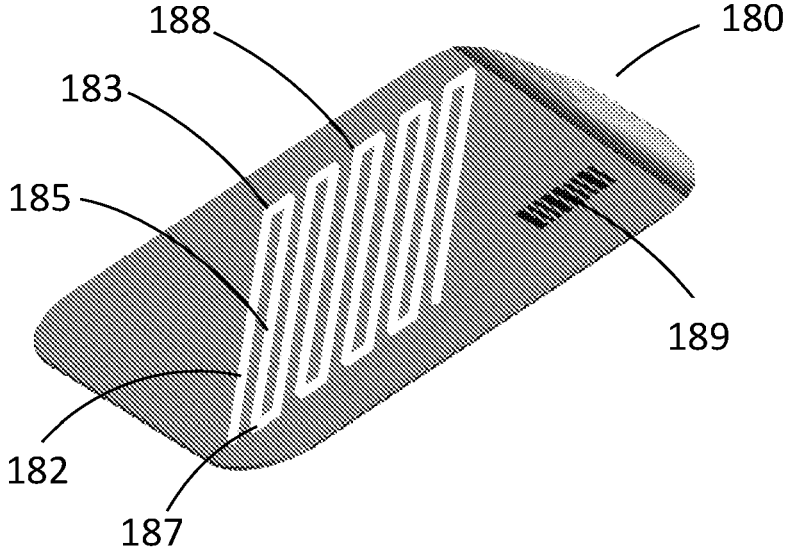
FIG. 14 is an isometric view of a smart card in accordance with another embodiment of the present invention.

In another embodiment, instead of using helical track component 150, a card 180 as illustrated in FIG. 14 can be used with adaptor 100. Card 180 includes a track 188 (such as a grooved track) which has different physical features to the rest of the card 180 in a similar way to card 60 discussed above. Track 188 is provided with oblique grooves 182, 185, rather than the axial and transverse grooves of card 60, and groove portions 183, 187 provide mechanical stops, thus affording the required interaction between the projecting ends of shaft 134 and card 180. The inclination of the grooves defines a dose rate, per unit of rotational movement, the axial length of the groove defining the dosage.

Track 188 of card 180 allows further dosages to be drawn and administered, the length of the track portions determining the amount of liquid to be drawn or administered at each step. In the present example, track 188 provides a common dosage and dosage rate at repeated intervals. However, in other examples, the track can provide for more than one dosage and/or more than one dosage rate. Card 180 also includes a barcode 189 (or other readable means) that can be used for scanning the card, as discussed in further detail below.

As will be understood, use of card 180 allows the card itself to directly govern the rate of advance of pin assembly 130 and allows more flexibility in customising dosage regimes for patients. However this embodiment requires track 188 to retain the ends of shaft 134, which can present technical challenges when using a thin, flexible card. In the alternative, employing helical track component 150 can provide a more reliable and robust drive of the axial movement of pin assembly 130, the movement governed by a card with an orthogonal groove arrangement.

It will be readily appreciated that other forms of a re-usable card may be provided. In one example, a card similar to card 60 can be provided but with no frangible portions. One or more cards of a similar nature may be provided, each card configured to provide a predetermined set dosage.

In one embodiment, a card, formed of a non-frangible material(s) is provided with a track in the form of a single linear slot or recess formed on the card. The pin may be placed at a first, terminal end of the slot or recess, with the pin then moved (in a similar manner as described in the embodiments above) along the slot or recess, until the pin engages a second, terminal end of the slot or recess. Thus, a set dosage may be drawn into the syringe, the dosage decided by the length of the slot or recess. Movement of the pin back along the slot or recess to the first, terminal end will thereby define expelling of the set dosage from the syringe. A kit can be provided with a plurality of different such cards, each with a slot or recess of a different length. The cards may be colour coded, the colour representing the length of the slot or recess and hence the corresponding set dosage. In this way, the user simply selects a card from the kit based on colour, so determining the dosage that will be administered.

Reference is now made to FIGS. 15A-15H, which show adaptor 1000 both separate to and coupled to a syringe 2000. It will be appreciated that adaptor 1000 functions in a similar manner to adaptor 10. The adaptor comprises a housing 1012 similar to housing 12. The x-y-z directions as defined above are similarly used with reference to the below description of this embodiment.

Extending perpendicularly outwardly from a side wall of housing 1012 in the x-direction is flange coupling portion 1018, which is adapted to attach to or support the flange 2012 of the barrel 2010 of the syringe 2000. Flange coupling portion 1018 provides support for housing 1012 when barrel 2010 and plunger 2014 are moved relative to one another whilst the adaptor 1000 is coupled to syringe 2000. Adaptor 1000 is connected to a plunger 2014 of syringe 2000 by a rigid linking member 1020, which at one end is received within housing 1012 and at the other end is connectable to the plunger. The end of linking member 1020 received within the housing is movable with a first pin assembly 1300 (as described below).

First pin assembly 1300 comprises two parts, an elongate arm 1332 and an oblique flap 1334 pivotally mounted thereto. Arm 1332 is substantially rectangular in shape as shown, having a pin 1337 extending therefrom (in the Z direction) within housing 1012. Arm 1332 may form part of or be separately connected to the end of linking member 1020. Linking member 1020 and first pin assembly 1300 are arranged to move with one another in the y-direction when plunger 2014 is moved relative to barrel 2010. Movement of pin 1337 is prevented in the x-direction by an underlying longitudinal slot 1032, such that movement of the pin 1337 is permitted only in the y-direction. Flap 1334 is pivotally mounted in a position as shown such as to engage a cam mechanism 1040, as described below.

A second pin assembly 1500 is located within housing 1012. The second pin assembly 1500 includes a body part (not shown) having a pin 1537 extending therefrom into housing 1012. Movement of the pin 1537 is constrained to the y-direction by an underlying longitudinal slot 1034. However, unlike pin 1337, which moves in direct relation with movement of arm 1332 (and hence plunger 2014), pin 1537 is arranged for independent movement, dictated by a mechanism that allows it to move in one direction along slot 1034 and in an incremental fashion.

Figures 15A, 15B:
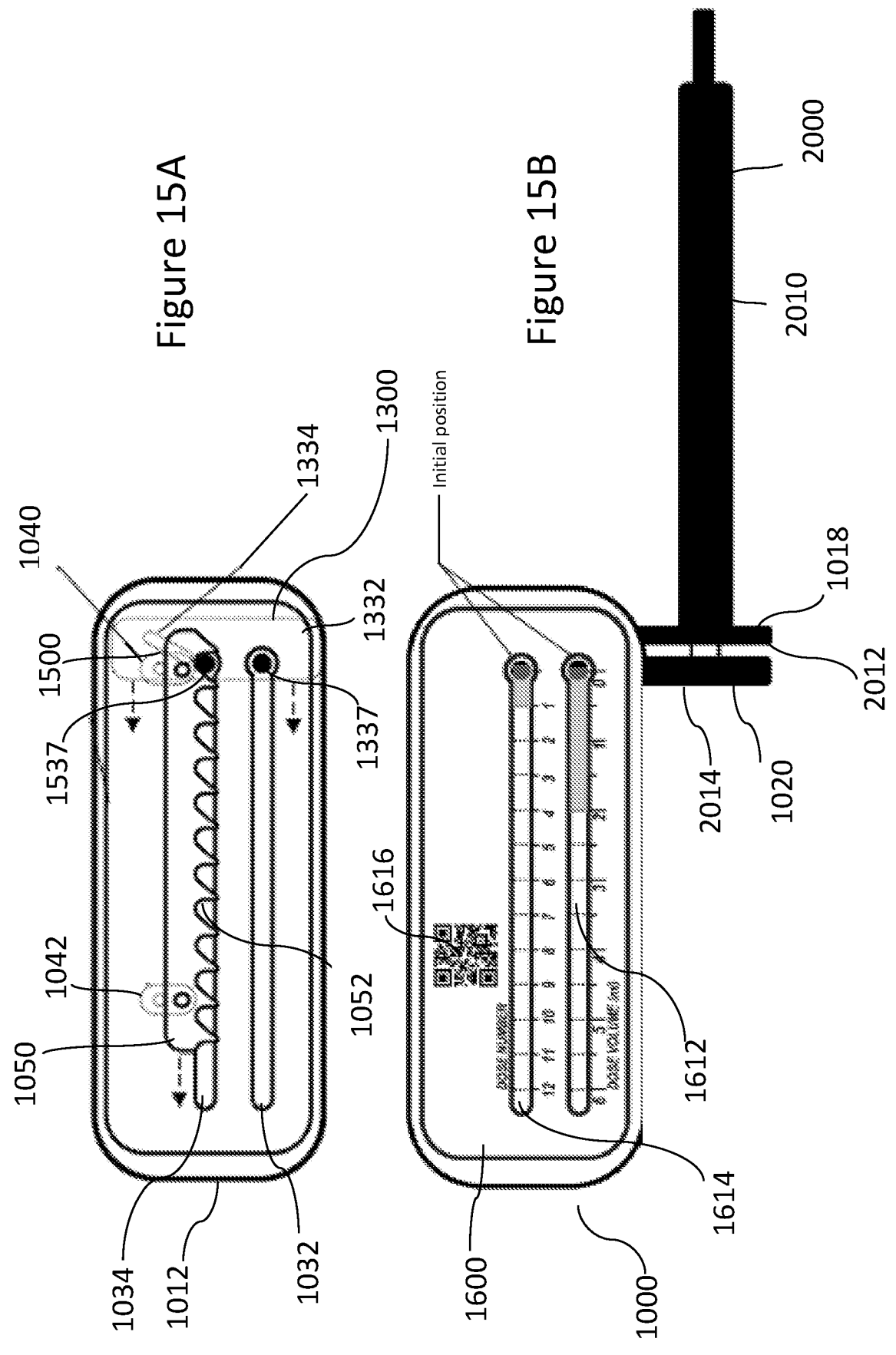
FIGS. 15A-15H illustrate plan views of an adaptor in accordance with a further embodiment of the invention in various operational states.

The mechanism to afford such limitation of movement includes a sawtooth rack 1050, extending in the y-direction. Sawtooth rack 1050 is rotationally mounted to housing 1012 by a first rotating cam mechanism 1040, mounted at a first end of rack 1050, and a second mechanism 1042 rotationally mounted to a second end of rack 1050. The teeth recesses 1052 of rack 1050 overlie slot 1034 when rack 1050 is in a home position (as shown in FIG. 15A). Pin 1537 is initially received within the first tooth recess 1052, being the rightmost tooth recess in FIG. 15A, and can then be moved incrementally to the recess of an adjacent tooth by way of operation of adaptor 1000.

In this embodiment, first pin assembly 1300 and its movement is associated with a dosage volume to be administered (in a similar way to the embodiments described above), with second pin assembly 1500 associated with the number of dosages delivered. Thus adaptor 1000 is configured to facilitate both the administering of a set dosage volume and provide an indication of (and a limit to) the number of dosages of that set dosage volume that are to be administered.

Figure 15C:
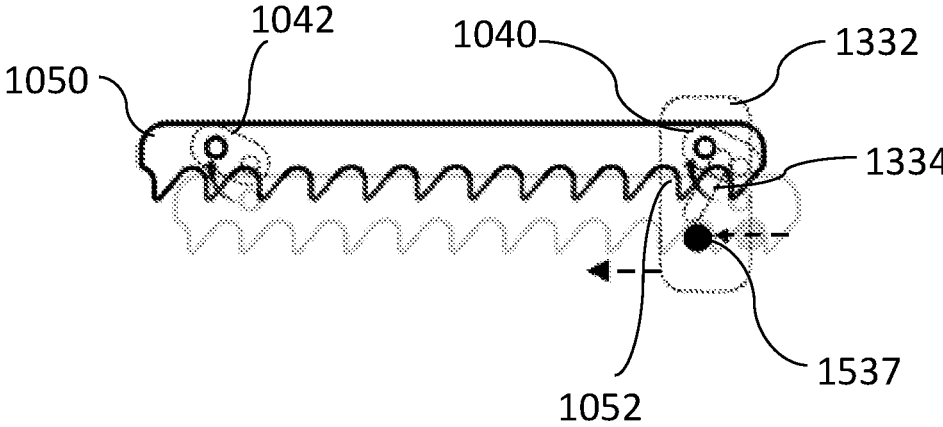
Figure 15D:
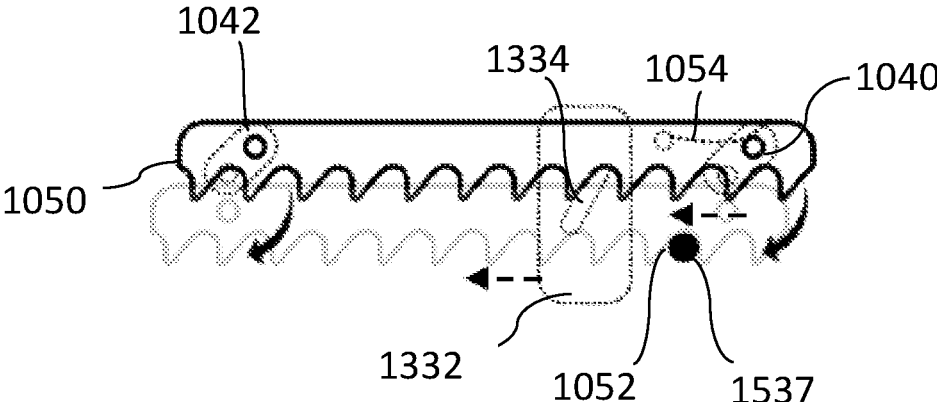
Figures 15E, 15F:
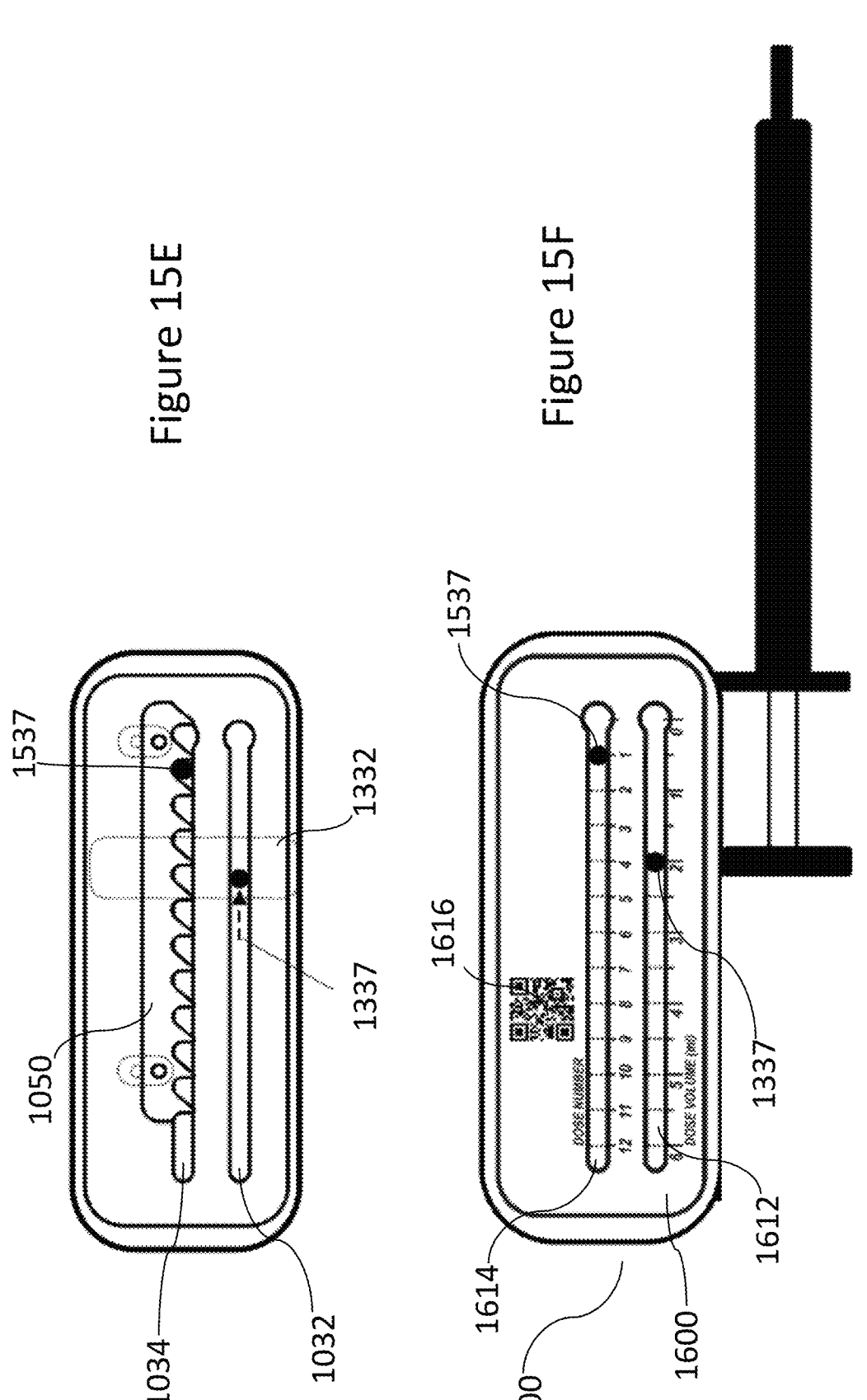
Figure 15G:
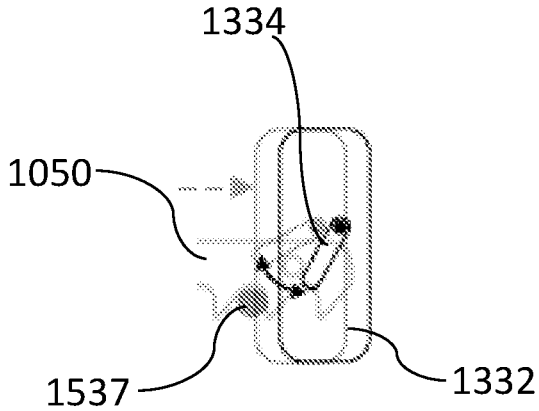

Movement of pin 1537 will now be described. When plunger 2014 is moved relative to barrel 2010 in order to draw in a volume of medicament, arm 1332 is moved from right to left, thereby drawing pin 1337 along slot 1032. This movement of arm 1332 will also result in the end of flap 1334, particularly the inward facing end of flap 1334, engaging with first cam mechanism 1040, causing its rotation clockwise (as shown in FIGS. 15C-15D) and hence resulting in clockwise rotation of both mechanisms 1040 and 1042 resulting in a rotational action on rack 1050 relative to housing 1012. This clockwise rotation of the rack, by way of action of the right-side edge of the tooth recess 1052, pushes pin 1537 in the y-direction (ie. towards the left) along slot 1034. This urging of the pin 1537 continues until the rack 1050 rotates sufficiently away from slot 1034 and therefore releases engagement with pin 1537. This action leaves pin 1537 having moved a certain, limited distance along slot 1034 whilst pin 1337 (carried by first pin assembly 1300) proceeds its movement along slot 1032 until it reaches its end position, corresponding to the intended dosage volume. A suitably positioned leaf spring 1054 (FIG. 15D) acts on first cam mechanism 1040 biasing rack 1050 towards slot 1034 so that, once it has completed a full revolution, it will be biased back into the home position. Once in the home position, pin 1537 is engaged in the next successive tooth recess 1052 of rack 1050 (as shown in FIG. 15E).

As arm 1332 (carried by assembly 1300) moves back in the y-direction (ie. from left to right), by movement of plunger 2014 towards barrel 2010 to expel the medicament, pin 1337 moves along with arm 1332 along slot 1032 and flap 1334 rotates to slip past pin 1537, thereby allowing arm 1332 (and pin 1337) to return to the initial position (FIGS. 15E-15G) ready to operate again in the same way for the next dosage.

Longitudinal movement of pins 1337 and 1537 in their respective slots are constrained by the introduction of a smart card 1600 into housing 1012. Card 1600 is inserted into housing 1012 by sliding card 1600 through a suitable opening in housing 1012 (card enters from right to left in FIG. 15B). Once received in housing 1012, card 1600 is engaged with the first and second pin assemblies so that pins 1337 and 1537 lie within the tracks of card 1600.

Card 1600 includes two tracks. A first track 1612 is in the form of a single longitudinal slot formed on the card. As indicated by the markings adjacent first track 1612, first track 1612 defines the predetermined, set dosage that can be withdrawn and expelled when card 1600 is operatively engaged with adaptor 1000. Card 1600 also includes a second track 1614, similarly in the form of a single longitudinal slot formed on the card. Second track 1614 is parallel with first track 1612. When card 1600 is in place, the first and second tracks 1612, 1614 are aligned with slots 1032, 1034 respectively. The length of first track 1612 defines the predetermined, set dosage that can be withdrawn and expelled when the card 1600 is operatively engaged with adaptor 1000, whilst the length of second track 1614 defines the number of dosages that can be withdrawn and expelled. As depicted in FIG. 15B, card 1600 is configured to allow for a single 2 ml dosage, i.e. a 2 ml dose to be administered once. Similar to the embodiments described above, physical features of card 1600 (in this case the ends of first and second tracks 1612, 1614) act to limit movement of plunger 2014 relative to the barrel 2010 of syringe 2000, due to pins 1337, 1537 engaging with the ends of the card tracks.

Thus, when pin 1337 encounters the end of first track 1612 (indicating a 2 ml dosage), pin 1337 is prevented from moving further along its slot and hence the plunger 2014 is prevented from further movement relative to barrel 2010. Thus, only the set 2 ml dosage can be drawn into the syringe. With movement of pin 1337 (under action of the mechanism described above), pin 1537 is moved incrementally one sawtooth position along its track, to the abutment end of second track 1614. Movement of arm 1332 back to its initial position will result in administration of the 2 ml dosage.

Figure 15H:
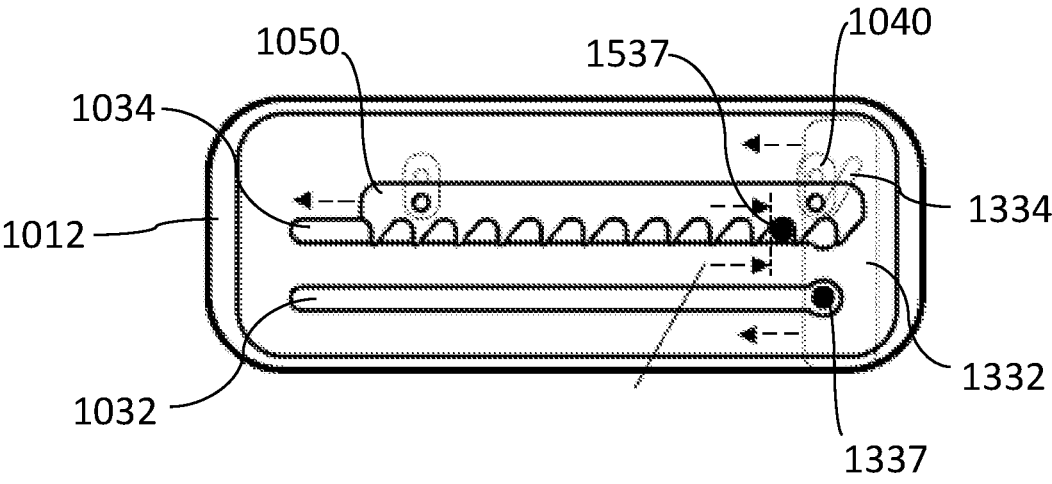

As card 1600 is intended to provide only a single dosage of the set dose volume, further attempts to draw and/or administer medicament are prevented by card 1600 as shown in FIG. 15H. If an attempt is made to move plunger 2014 away from barrel 2010 in order to draw the medicament, pin 1537 can move no further as it has reached the end of the second track 1514, hence preventing movement. Thus, the possibility of administering a second dosage is prevented.

The card is made so that the length of each track required can be punched out, by removing a portion of each track. The portion punched out (the shaded portions in FIG. 15B) indicating the prescribed dosage volume and the number of dosages to be administered. The card can then be inserted into adaptor 1000 for administration of the medication. The card also includes a suitable encoding element 1616. The encoding element 1616 can be a readable QR code or barcode, or maybe an RFID tag or other remotely readable data store.

As will be understood, this embodiment provides the ability to guide or limit not only the dose but the number of repeats of that dose. The movement of the second pin 1537 along its track provides both an indicator to the user of the number of doses administered and a means of limiting that number of doses.

Method of Use

The steps below set out an example of a method of use of the invention for administering a liquid dose to a child, e.g. a simple analgesic such as ibuprofen or paracetamol.

1. Medication and dosage is prescribed by a medical practitioner.
2. The prescription is presented at a pharmacy and scanned. The scanned data is input to software which verifies the medication and dose and controls the dispensing of the medication in a vial or similar bearing a medication barcode. Along with the medicine, the software and suitable connected hardware prints a small individualised single-use plastic key card, encoded with data recording, inter alia, patient identity, medicine and dose, the data relating to the dispensing event being uploaded to a remote electronic medication system (EMS) for recordal. The encoding can be by way of a readable QR code or barcode, or maybe an RFID tag or other remotely readable data store.
3. At the ward, a nurse uses a scanner to read the key card, the child's wrist identifier and the medication barcode into suitable software, in order to verify the intended administration of the dose via the EMS.
4. The adaptor (10 or 100) is attached to the syringe, and the key card inserted. As discussed above, the card controls the volume of medication to be administered and the child is safely dosed. The EMS registers the key card as expired and it thus cannot be used again and is discarded.
5. The information regarding the administration is automatically uploaded to the EMS to record all the details relevant to the administration event, including the time of administration.

The method can also include steps of photographing the smart card after use, which when uploaded to the EMS, provides further evidence that the dosage has been administered.

The invention therefore provides integration of smart cards, a governing device and software to accurately and safely deliver accurate doses and the correct number of doses, along with provision and storage of digital records relating to activities relating to the dosage. This approach therefore affords the prevention of error at the calculation and dispensing stages as well as at the administration stage.

It will be understood that the invention disclosed and defined in this specification extends to all alternative combinations of two or more of the individual features mentioned or evident from the text or drawings. All of these different combinations constitute various alternative aspects of the invention.

The embodiments described above are designed for use with liquid medicaments, e.g. oral medicines for administration to neonates ('infant drops') or injectable medication. However the invention can equally be applied to the dispensing and administration of solid form medicaments, such as pills, tablets or capsules. In such an application a mechanism of the sort described herein is used to control delivery of the required number of pills, tablets or capsules from a dispensing container.

The invention claimed is:

1. An adaptor for a medicament delivery device, the adaptor configured to enable a set dosage of a medicament to be drawn into and/or expelled from the device, the adaptor including:

a body configured to be coupled to the device;

an attachment portion movable with respect to the body and configured for attachment with a first part of the device;

an engaging portion movable with the attachment portion; and a receiver configured to receive an insertable and removable movement constraint guide (MCG) and facilitate engagement between the engaging portion and the MCG;

wherein the MCG includes one or more physical features defining at least an aspect of the set dosage, the one or more physical features of the MCG including one or more tracks for guiding longitudinal and transverse movement of a part of said engaging portion and thus movement of said first part of the device, said MCG being a suitably shaped card; and wherein activation of said first part of the device to draw and/or expel the medicament is stopped when the set dosage is reached by engagement between the engaging portion and at least one of the one or more physical features of the MCG.

2. The adaptor of claim 1, wherein the device is a syringe for delivery of the medicament in fluid form, said first part of the device being a syringe plunger, wherein the activation of said first part of the device being movement of the syringe plunger.

3. The adaptor of claim 1, wherein the MCG is a planar element, the receiver having a complementary shaping to receive said element.

4. The adaptor of claim 1, wherein the engaging portion and the attachment portion are provided as a single unit, selected from the group of an integral unit and an assembly of parts.

5. The adaptor of claim 1, wherein the set dosage is a single dose or a prescribed dosing regime whereby the MCG is configured to delimit more than one dose.

6. The adaptor of claim 1, wherein the engaging portion is adapted to be directly coupled to the attachment portion.

7. The adaptor of claim 1, wherein the one or more physical features are protrusions or recesses on a surface of the MCG that provide abutment surfaces for the engaging portion.

8. The adaptor of claim 1, wherein the MCG includes one or more smart features configured to provide patient specific information to an external device.

9. The adaptor of claim 1, wherein the engaging portion is a first engaging portion, and wherein the adaptor includes a second engaging portion movable in relation to the first engaging portion and configured to engage one or more additional physical features of the MCG.

10. The adaptor of claim 9, wherein engagement between the second engaging portion and the one or more additional physical features of the MCG provides a different aspect of the set dosage to engagement between the first engaging portion and the one or more physical features of the MCG.

11. The adaptor of claim 9, wherein the one or more tracks of the MCG comprise a first track and a second track, the first engaging portion is configured to move along the first track of the MCG and the second engaging portion is configured to move along the second track of the MCG, wherein the first track defines a dosage volume of the set dosage and the second track defines a number of dosages of the set dosage.

12. The adaptor of claim 11, wherein the adaptor includes a retaining structure mounted to the body, adjacent the second track, the retaining structure configured to limit the second engaging portion to incremental movement along said second track, each increment associated with one dosage.

13. The adaptor of claim 12, wherein the retaining structure is a sawtooth rack, the incremental movement of the second engaging portion being controlled by the interaction between the second engaging portion and the successive teeth of the sawtooth rack.

14. The adaptor of claim 1, further including the MCG.

* * * * *